(12) United States Patent
Matsui et al.

(10) Patent No.: US 11,199,457 B2
(45) Date of Patent: Dec. 14, 2021

(54) MEASURING INSTRUMENT FOR PHYSIOLOGICAL HEAT QUANTITY

(71) Applicants: DENSO CORPORATION, Kariya (JP); TOYOTA JIDOSHA KABUSHIKI KAISHA, Toyota (JP)

(72) Inventors: Hirohito Matsui, Nisshin (JP); Toshikazu Harada, Kariya (JP); Norihito Higo, Kariya (JP)

(73) Assignees: DENSO CORPORATION, Kariya (JP); TOYOTA JIDOSHA KABUSHIKI KAISHA, Toyota (JP)

( * ) Notice: Subject to any disclaimer, the term of this patent is extended or adjusted under 35 U.S.C. 154(b) by 216 days.

(21) Appl. No.: 16/514,123

(22) Filed: Jul. 17, 2019

(65) Prior Publication Data
US 2019/0339138 A1 Nov. 7, 2019

Related U.S. Application Data

(63) Continuation of application No. PCT/JP2017/042819, filed on Nov. 29, 2017.

(30) Foreign Application Priority Data

Jan. 25, 2017 (JP) ............................. JP2017-011595

(51) Int. Cl.
*G01K 17/00* (2006.01)
*A61B 5/01* (2006.01)
(Continued)

(52) U.S. Cl.
CPC ................ *G01K 17/00* (2013.01); *A61B 5/01* (2013.01); *A61B 5/4866* (2013.01);
(Continued)

(58) Field of Classification Search
CPC .......... G01K 17/00; G01K 13/20; A61B 5/01; A61B 5/4866; A61B 5/6801; A61B 2562/0271; A61B 2562/164
See application file for complete search history.

(56) References Cited

U.S. PATENT DOCUMENTS

| | | | |
|---|---|---|---|
| 5,524,618 | A | 6/1996 | Pottgen et al. |
| 5,813,994 | A | 9/1998 | Pottgen et al. |

(Continued)

FOREIGN PATENT DOCUMENTS

| | | | |
|---|---|---|---|
| JP | 2004153128 A | 5/2004 | |
| JP | 2004267788 A | 9/2004 | |

(Continued)

OTHER PUBLICATIONS

JP 2017-023408A (English Translation) (Year: 2017).*

*Primary Examiner* — Daniel L Cerioni
(74) *Attorney, Agent, or Firm* — Harness, Dickey & Pierce, P.L.C.

(57) ABSTRACT

An measuring instrument for a physiological heat quantity emitted from a human body includes a heat flux sensor, and a calculator. The heat flux sensor includes a sensor main body portion and a moisture absorbing member. The sensor main body portion has multiple through holes penetrating through the sensor main body portion from a first surface to a second surface. The sensor main body portion is disposed on a human body such that the first surface is adjacent to the human body when in use, and outputs a sensor signal according to a heat flux passing through the sensor main body portion from the first surface toward the second surface. The moisture absorbing member is stacked on the second surface of the sensor main body portion. The calculator calculates the physiological heat quantity based on the sensor signal.

7 Claims, 11 Drawing Sheets

(51) Int. Cl.
*A61B 5/00* (2006.01)
*G01K 13/20* (2021.01)

(52) U.S. Cl.
CPC ............ *A61B 5/6801* (2013.01); *G01K 13/20* (2021.01); *A61B 2562/0271* (2013.01); *A61B 2562/164* (2013.01)

(56) References Cited

U.S. PATENT DOCUMENTS

2015/0144171 A1    5/2015  Taniguchi et al.
2016/0162256 A1*  6/2016  Komaromi ............. A61B 5/681
                                                                   700/94
2017/0049397 A1*  2/2017  Sun .......................... A61B 5/01

FOREIGN PATENT DOCUMENTS

| | | |
|---|---|---|
| JP | 2012079841 A | 4/2012 |
| JP | 2014007376 A | 1/2014 |
| JP | 5523985 B2 | 6/2014 |
| JP | 5573565 B2 | 8/2014 |
| JP | 2015144212 A | 8/2015 |
| JP | 2017023408 A * | 2/2017 |
| WO | WO-2018139040 A1 | 8/2018 |

* cited by examiner

US 11,199,457 B2

MEASURING INSTRUMENT FOR PHYSIOLOGICAL HEAT QUANTITY

CROSS REFERENCE TO RELATED APPLICATIONS

The present application is a continuation application of International Patent Application No. PCT/JP2017/042819 filed on Nov. 29, 2017, which designated the United States and claims the benefit of priority from Japanese Patent Application No. 2017-011595 filed on Jan. 25, 2017. The entire disclosures of all of the above applications are incorporated herein by reference.

TECHNICAL FIELD

The present disclosure relates to a measuring instrument for measuring a physiological heat quantity.

BACKGROUND

For example, a thermoelectric conversion device can be used as a heat flux sensor.

SUMMARY

The present disclosure describes a measuring instrument for measuring a physiological heat quantity emitted from a human body. The measuring instrument includes a heat flux sensor to be disposed on a surface of the human body when in use, and a calculator configured to calculate the physiological heat quantity. The heat flux sensor includes a film-shaped sensor main body portion and a film-shaped moisture absorbing member capable of absorbing sweat and releasing the absorbed sweat.

BRIEF DESCRIPTION OF DRAWINGS

The above and other objects, features and advantages of the present disclosure will become more apparent from the following detailed description made with reference to the accompanying drawings, in which.

DETAILED DESCRIPTION

Figure 1:
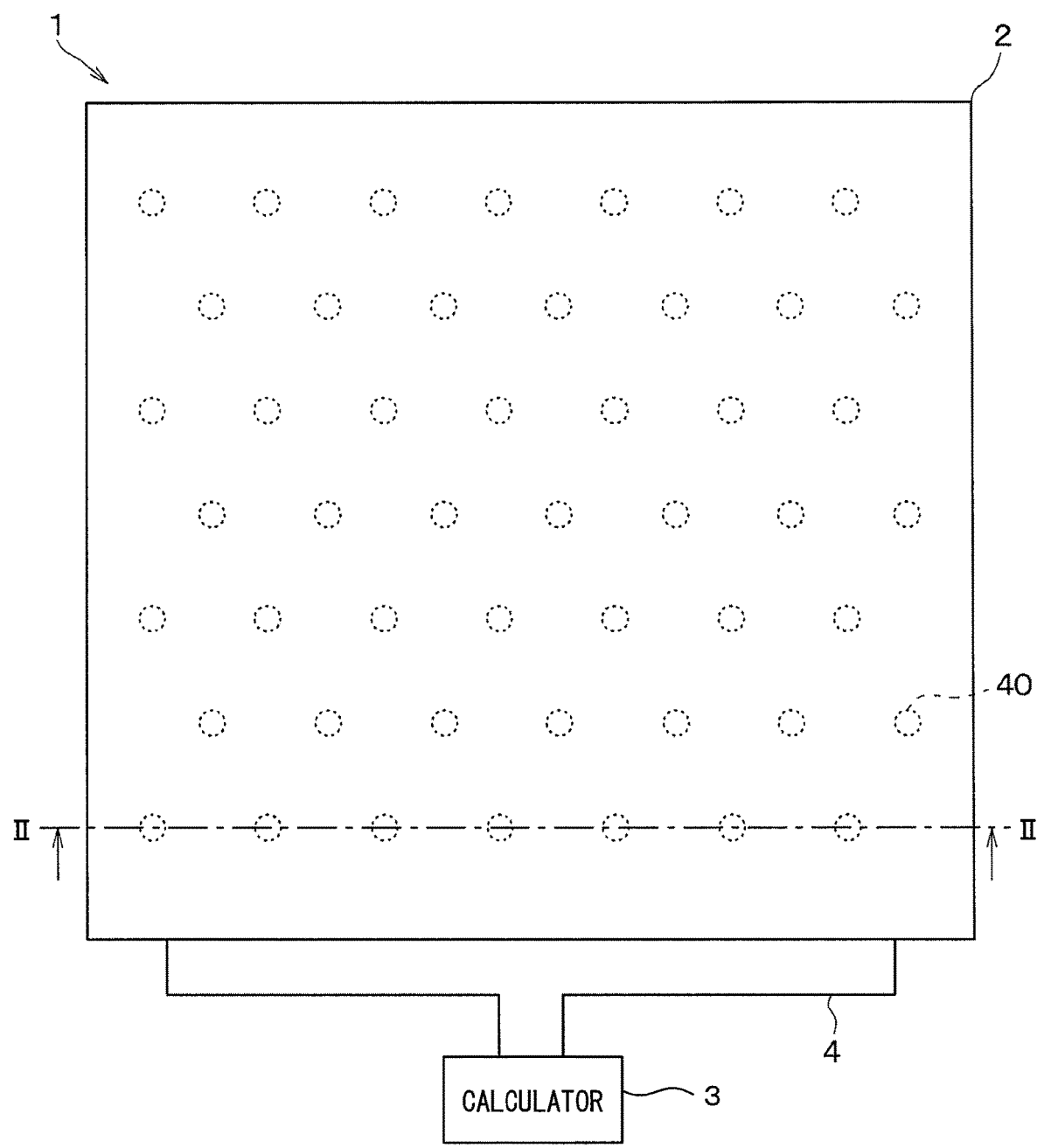
FIG. 1 is a diagram showing an overall configuration of a measuring instrument for a physiological heat quantity according to a first embodiment.

It is conceivable to attach a heat flux sensor on a surface of a human body in order to measure a physiological heat quantity emitted from a human body. In such a case, if sweat accumulates between the heat flux sensor and a skin, a person to be measured is likely to feel uncomfortable. In order to accurately measure the physiological heat quantity emitted from the human body, there may be a need to measure both the heat quantity of convection component emitted from the human body to air and the heat quantity used for latent heat of evaporation when sweat evaporates on the surface of the human body.

According to an embodiment of the present disclosure, a measuring instrument for measuring a physiological heat quantity emitted from a human body includes a heat flux sensor to be attached to a surface of the human body, and a calculator configured to calculate the physiological heat quantity. The heat flux sensor includes a film-shaped sensor main body portion and a film-shaped moisture absorbing member capable of absorbing sweat and releasing the absorbed sweat. The sensor main body portion has a first surface and a second surface on the opposite side of the first surface. The sensor main body portion is formed with a plurality of through holes that penetrate through the sensor main body portion from the first surface to the second surface. The sensor main body portion is to be disposed on the surface of the human body such that the first surface is adjacent to the human body when in use. The moisture absorbing member is stacked on the second surface of the sensor main body portion. The sensor main body portion is configured to output a sensor signal according to a heat flux passing through the sensor main body portion from the first surface toward the second surface. The calculation unit is configured to calculate the physiological heat quantity emitted from the human body based on the sensor signal.

According to the above configuration, in a state in which the heat flux sensor is attached to a surface of the human body, sweat generated on the surface of the human body is allowed to move toward the second surface of the sensor main body portion through the multiple through holes. As such, it is less likely that a person to be measured will feel uncomfortable due to sweat.

Further, the heat flux sensor can evaporate sweat from the second surface of the sensor main body portion by means of the multiple through holes and the moisture absorbing member. For that reason, both the thermal energy of convection component and the thermal energy of the latent heat of evaporation are allowed to pass through the sensor main body portion. Therefore, it is possible to measure the heat quantity used for both convection and latent heat of evaporation by using the heat flux sensor. According to the above measuring instrument, the physiological heat quantity emitted from the human body can be accurately measured.

Embodiments of the present disclosure will be further described hereinafter with reference to the drawings. In the following descriptions, the same or equivalent parts in the respective embodiments are designated with the same reference numerals.

First Embodiment

Figure 2:
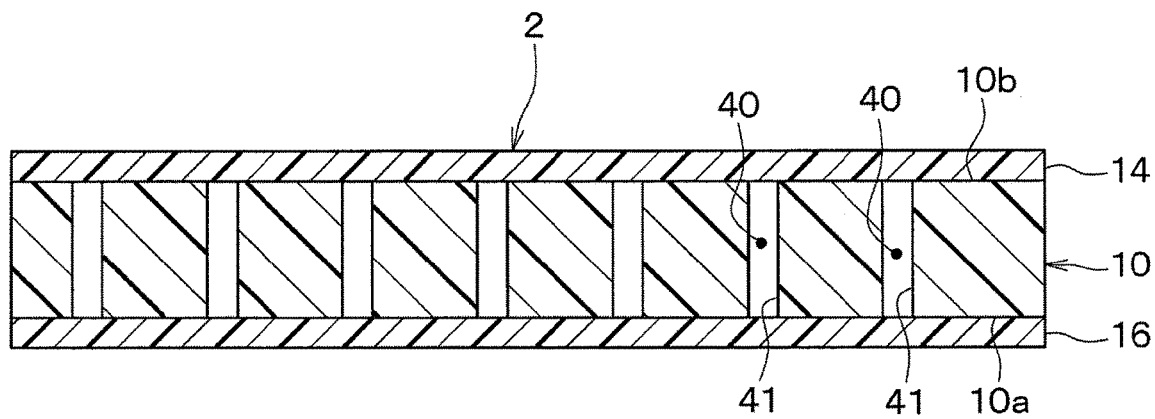
FIG. 2 is a cross-sectional view taken along a line II-II of a heat flux sensor shown in FIG. 1.

A measuring instrument 1 shown in FIGS. 1 and 2 measures a physiological heat quantity emitted from a human body. The physiological heat quantity is the quantity of heat consumed in association with an activity of an organism, and is also called calorie consumption.

As shown in FIG. 1, the measuring instrument 1 includes a heat flux sensor 2 and a calculator 3.

The heat flux sensor 2 is to be attached on a surface of the human body. The heat flux sensor 2 detects a heat flux emitted from the human body. The heat flux is the quantity of heat flowing through a unit area per unit time. The heat flux sensor 2 is in the form of a film. A planar shape of the heat flux sensor 2 is a square.

The calculator 3 is connected to the heat flux sensor 2 through a wiring 4. The calculator 3 receives a sensor signal from the heat flux sensor 2. The calculator 3 calculates the physiological heat quantity emitted from the human body based on a value of the sensor signal. For example, the calculator 3 calculates a heat flux based on the sensor signal. The calculator 3 converts the calculation result into units as necessary, and calculates the physiological heat quantity. The calculator 3 may directly calculate the physiological heat quantity of the unit to be obtained based on the sensor signal. In this case, the calculator 3 calculates the physiological heat quantity based on the value of the sensor signal and a relationship between the value of the sensor signal and the quantity of heat emitted from the human body.

As shown in FIG. 2, the heat flux sensor 2 includes a sensor main body portion 10, a first moisture absorbing member 14, and a second moisture absorbing member 16.

The sensor main body portion 10 is in the form of a film. The sensor main body portion 10 has a first surface 10a and a second surface 10b on the opposite side of the first surface 10a. The sensor main body portion 10 is formed with multiple through holes 40 penetrating through the sensor main body portion 10 from the first surface 10a to the second surface 10b.

Each of the through holes 40 has a circular shape on the first surface 10a and on the second surface 10b as shown in FIG. 1. The through hole 40 is a portion defining a through space surrounded by a cylindrical inner wall surface 41. The inner wall surface 41 is a space defining portion that defines the through space. The inner wall surface 41 is formed in the sensor main body portion 10.

The sensor main body portion 10 is attached to the human body such that the first surface 10a of the sensor main body portion 10 is adjacent to the human body than the second surface 10b. The sensor main body portion 10 outputs a sensor signal according to the heat flux passing through the sensor main body portion 10 from the first surface 10a toward the second surface 10b. A specific configuration of the sensor main body portion 10 will be described later.

The first moisture absorbing member 14 and the second moisture absorbing member 16 are each in a film shape. The first moisture absorbing member 14 and the second moisture absorbing member 16 have hygroscopic properties. The hygroscopicity of each of the first moisture absorbing member 14 and the second moisture absorbing member 16 is higher than that of the sensor main body portion 10. The first moisture absorbing member 14 and the second moisture absorbing member 16 can absorb sweat and release the absorbed sweat.

Figure 3:
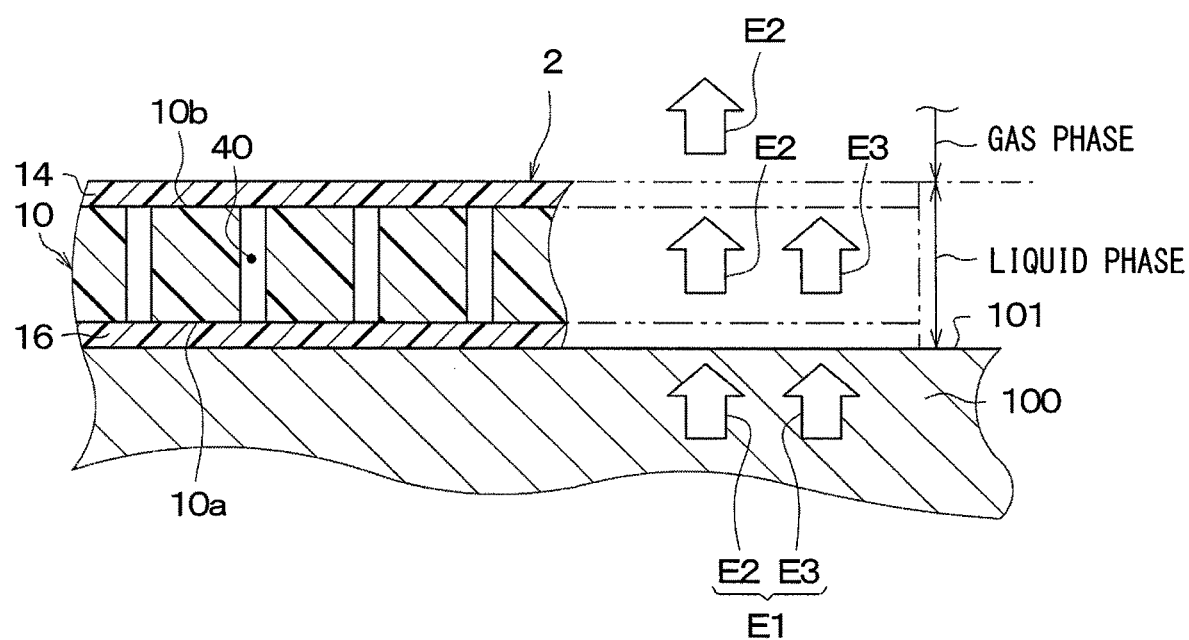
FIG. 3 is a cross-sectional view of the heat flux sensor shown in FIG. 1, which shows a state in which the heat flux sensor is attached to a surface of a human body.

The first moisture absorbing member 14 is stacked on the second surface 10b of the sensor main body portion 10. As shown in FIG. 3, in a state in which the heat flux sensor 2 is attached on the surface 101 of the human body 100, the first moisture absorbing member 14 is located on a side away from the human body 100 with respect to the sensor main body portion 10.

The second moisture absorbing member 16 is stacked on the first surface 10a of the sensor main body portion 10. As shown in FIG. 3, in a state in which the heat flux sensor 2 is attached on the surface 101 of the human body 100, the second moisture absorbing member 16 is located between the surface 101 of the human body 100 and the sensor main body portion 10.

The second moisture absorbing member 16 absorbs sweat generated on the surface 101 of the human body 100, and disperses the absorbed sweat into each of the multiple through holes 40. The second moisture absorbing member 16 allows the sweat generated on the surface 101 of the human body 100 to easily move in a direction along the surface 101 of the human body 100.

The first moisture absorbing member 14 evaporates the sweat suctioned onto the second surface 10b of the sensor main body portion 10 through the multiple through holes 40 and discharges the sweat into the air. The first moisture absorbing member 14 covers all of the multiple through holes 40.

As the first moisture absorbing member 14 and the second moisture absorbing member 16, members each made of a porous material are used. In that case, both the first moisture absorbing member 14 and the second moisture absorbing member 16 have multiple pores inside. A part of the multiple pores continues in a direction intersecting with the first surface 10a and the second surface 10b. A part of the multiple pores continues in a direction along the first surface 10a and the second surface 10b. As the first moisture absorbing member 14 and the second moisture absorbing member 16, any other member can be used as long as the member can absorb sweat and release the absorbed sweat and retain a film-like shape.

Next, a specific structure of the sensor main body portion 10 will be described with reference to FIGS. 4, 5, and 6. As shown in FIGS. 5 and 6, the sensor main body portion 10 includes an insulation member 12, multiple first thermoelectric members 18, multiple second thermoelectric members 20, multiple first conductor patterns 22, and multiple second conductor patterns 24.

The insulation member 12 has a film shape and has a first surface 12a and a second surface 12b on opposite sides. The first surface 12a of the insulation member 12 defines the first surface 10a of the sensor main body portion 10. The second surface 12b of the insulation member 12 defines the second surface 10b of the sensor main body portion 10. An orientation of the insulation member 12 in the vertical direction shown in FIGS. 5 and 6 is opposite to an orientation of the insulation member 12 in the vertical direction shown in FIGS. 2 and 3. The insulation member 12 is made of an insulating material having flexibility. As the insulating material, a thermoplastic resin is used.

The multiple first thermoelectric members 18 are disposed inside the insulation member 12. The multiple first thermoelectric members 18 are made of a first thermoelectric material. The multiple second thermoelectric members 20 are disposed inside the insulation member 12. The multiple second thermoelectric members 20 are made of a second thermoelectric material different from the first thermoelectric material. As the first thermoelectric material and the second thermoelectric material, a semiconductor material or a metal material is used. In the direction along the first surface 12a and the second surface 12b of the insulation member 12, the multiple first thermoelectric members 18 and the multiple second thermoelectric members 20 are alternately arranged.

The multiple first conductor patterns 22 are connection members each for connecting the first thermoelectric member 18 and the second thermoelectric member 20 that are adjacent to each other among the multiple first thermoelectric members 18 and the multiple second thermoelectric members 20. The multiple first conductor patterns 22 are disposed adjacent to the first surface 12a of the insulation member 12 with respect to the multiple first thermoelectric members 18 and the multiple second thermoelectric members 20.

The multiple second conductor patterns 24 are connection members each for connecting the first thermoelectric member 18 and the second thermoelectric member 20 arranged adjacent to each other among the multiple first thermoelectric members 18 and the multiple second thermoelectric members 20. The multiple second conductor patterns 24 are disposed adjacent to the second surface 12b of the insulation member 12 with respect to the multiple first thermoelectric members 18 and the multiple second thermoelectric members 20.

The multiple first conductor patterns 22 and the multiple second conductor patterns 24 are formed of conductor films each having a desired planar shape. As the conductor film, a metal thin film is used.

In the present embodiment, the insulation member 12 includes a base material 26, a first protective member 28, and a second protective member 30.

Each of the base material 26, the first protective member 28, and the second protective member 30 has a film shape. Each of the base material 26, the first protective member 28, and the second protective member 30 is made of a thermoplastic resin having flexibility. The base material 26, the first protective member 28, and the second protective member 30 may be made of a resin material having flexibility other than thermoplastic resin or an insulating material having flexibility other than resin material.

The base material 26 has a first surface 26a and a second surface 26b opposite to the first surface 26a. The base material 26 is formed with multiple first through holes 261 and multiple second through holes 262 penetrating in a thickness direction of the base material 26. The multiple first through holes 261 and the multiple second through holes 262 penetrate through the base material 26 from the first surface 26a to the second surface 26b. The first thermoelectric member 18 is disposed in the first through holes 261. The second thermoelectric member 20 is disposed in the second through holes 262.

The first protective member 28 is stacked on the first surface 26a of the base material 26. The first protective member 28 has a surface 28b adjacent to the base material 26 and a surface 28b on the side opposite to the base material 26. The opposite surface 28b defines the first surface 12a of the insulation member 12.

The second protective member 30 is stacked on the second surface 26b of the base material 26. The second protective member 30 has a surface 30a adjacent to the base material 26 and a surface 30b on the side opposite to the base material 26. The opposite surface 30b defines the second surface 12b of the insulation member 12.

The multiple first conductor patterns 22 are disposed between the first surface 26a of the base material 26 and the first protective member 28. The multiple second conductor patterns 24 are disposed between the second surface 26b of the base material 26 and the second protective member 30. In this manner, the multiple first conductor patterns 22 and the multiple second conductor patterns 24 are disposed inside the insulation member 12.

A heat flow passes through the sensor main body portion 10 in a direction from one of the first surface 10a and the second surface 10b of the sensor main body portion 10 toward the other. At this time, a temperature difference occurs between the first surface 10a side and the second surface 10b side of the sensor main body portion 10. In other words, a temperature difference occurs between one side and the other side of each of the first thermoelectric member 18 and the second thermoelectric member 20 connected to each other. As a result, a thermoelectromotive force is generated in the first thermoelectric member 18 and the second thermoelectric member 20 by the Seebeck effect. The sensor main body portion 10 outputs the thermoelectromotive force, specifically, the voltage, as a sensor signal. In this manner, the sensor main body portion 10 outputs a sensor signal corresponding to a magnitude of the heat flux of the heat flow passing through the sensor main body portion 10.

Figure 4:
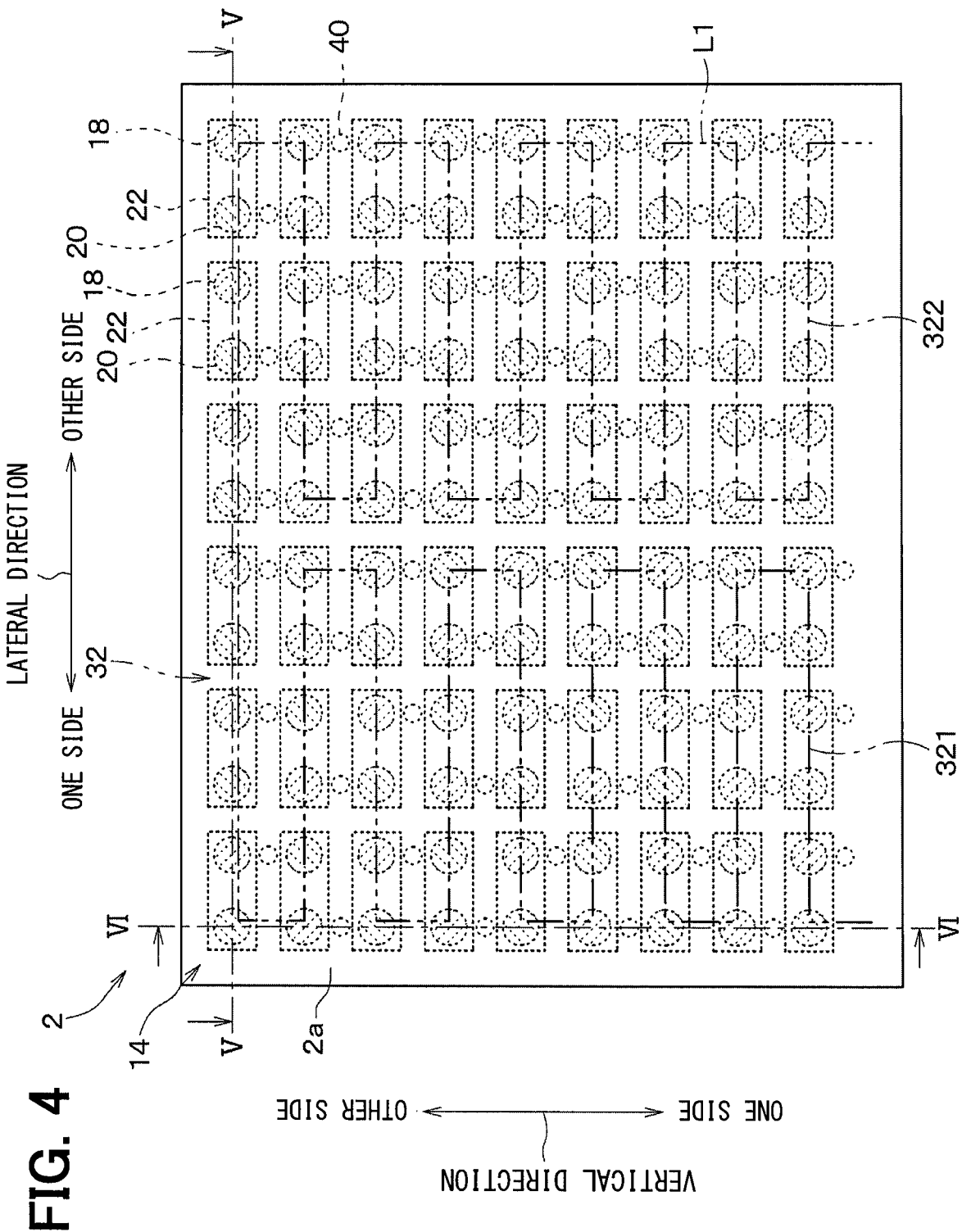
FIG. 4 is a plan view of the heat flux sensor according to the first embodiment.
Figure 5:
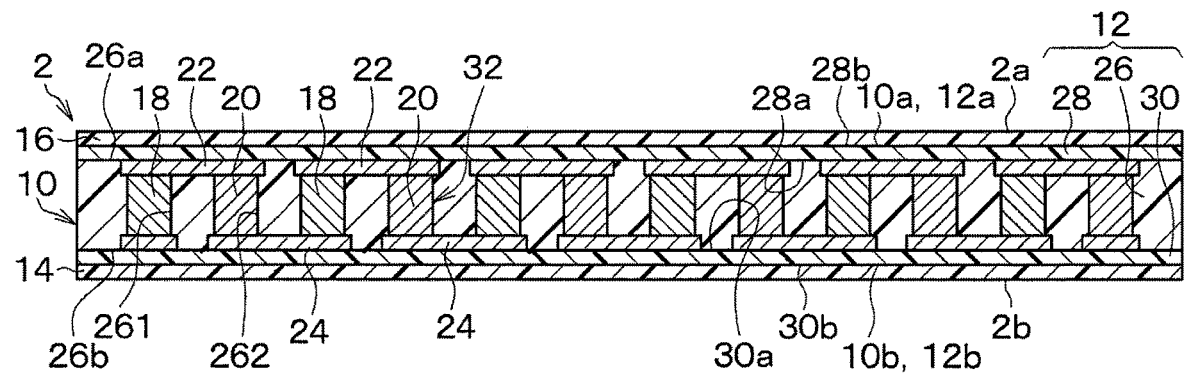
FIG. 5 is a cross-sectional view taken along a line V-V in FIG. 4.
Figure 6:
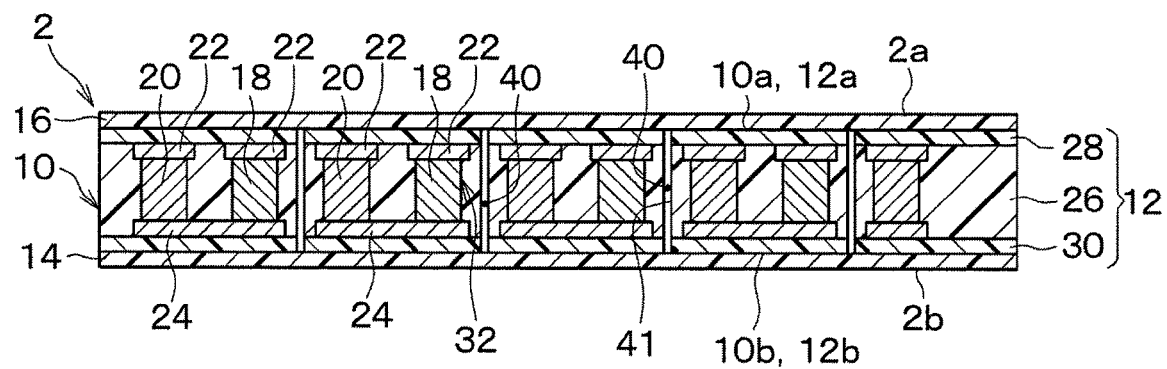
FIG. 6 is a cross-sectional view taken along a VI-VI line in FIG. 4.

As shown in FIGS. 4, 5, and 6, a conductor portion 32 is formed by connecting the multiple first thermoelectric members 18, the multiple second thermoelectric members 20, the multiple first conductor patterns 22, and the multiple second conductor patterns 24. In the conductor portion 32, the first thermoelectric member 18, the first conductor pattern 22, the second thermoelectric member 20, and the second conductor pattern 24 are repeatedly connected in series in a stated order. In FIG. 4, a state in which the conductor portions 32 are connected to each other is indicated by a two-dot chain line L1.

As shown in FIG. 4, the conductor portion 32 has a meandering shape in a direction along the first surface 12a and the second surface 12b of the insulation member 12. A shape of the conductor portion 32 matches a shape projected when the conductor portion 32 is projected onto a predetermined plane in the thickness direction of the insulation member 12. The predetermined plane is, for example, the first surface 12a of the insulation member 12.

In this example, an up and down direction in FIG. 4 is defined as a vertical direction. A left and right direction in FIG. 4 is defined as a lateral direction. At this time, the conductor portion 32 has a first conductor portion 321 which is one side of the conductor portion 32 in the lateral direction, and a second conductor portion 322 which is the other side of the conductor portion 32 in the lateral direction. The left side of FIG. 4 corresponds to one side in the lateral direction. The right side of FIG. 4 corresponds to the other side in the lateral direction.

The first conductor portion 321 has a meandering shape so as to proceed from one side in the vertical direction to the other side while alternately swinging to one side in the horizontal direction and the other side. A lower side of FIG. 4 corresponds to one side in the vertical direction. The upper side of FIG. 4 corresponds to the other side in the vertical direction.

The second conductor portion 322 has a meandering shape that moves from one side in the vertical direction to the other side while alternately swinging to one side in the horizontal direction and the other side so that the swinging side in the horizontal direction is opposite to the first conductor portion 321. The first conductor portion 321 and the second conductor portion 322 are connected to each other on the other side in the vertical direction.

As shown in FIG. 6, each of the multiple through holes 40 penetrates through the insulation member 12 from the first surface 12a to the second surface 12b of the insulation member 12. Each of the multiple through holes 40 is formed in a region of the insulation member 12 where the first thermoelectric member 18, the second thermoelectric member 20, the first conductor pattern 22, and the second conductor pattern 24 are not disposed.

Next, a manufacturing process of the heat flux sensor 2 according to the present embodiment will be described with FIG. 7A to FIG. 7H. FIGS. 7A to 7H correspond to cross-sectional views of the heat flux sensor 2 shown in FIG. 6.

Figure 7A:
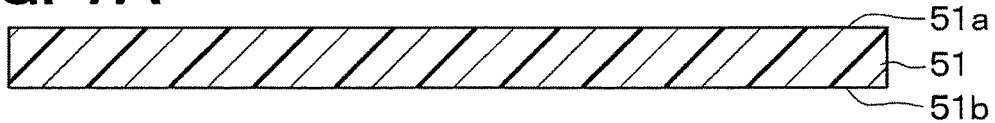
FIG. 7A is a cross-sectional view showing a process for manufacturing the heat flux sensor according to the first embodiment.

As shown in FIG. 7A, a film-shaped base material 51 is prepared. The base material 51 has a first surface 51a and a second surface 51b opposite to the first surface 51a.

Figure 7B:
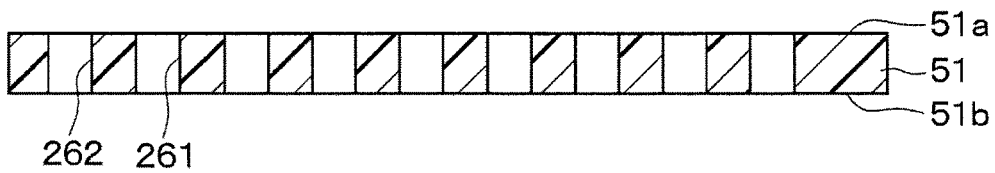
FIG. 7B is a cross-sectional view showing a process for manufacturing the heat flux sensor subsequent to FIG. 7A.

Subsequently, as shown in FIG. 7B, multiple first through holes 261 and multiple second through holes 262 are formed in the base material 51. The multiple first through holes 261 and the multiple second through holes 262 penetrate through the base material 51 from the first surface 51a to the second surface 51b. The first through holes 261 and the second through holes 262 are alternately arranged.

Figure 7C:
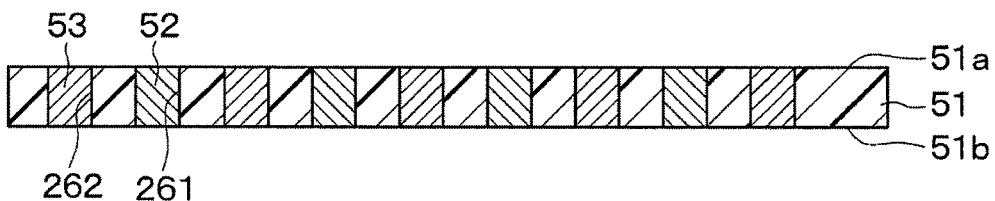
FIG. 7C is a cross-sectional view showing a process for manufacturing the heat flux sensor subsequent to FIG. 7B.

Subsequently, as shown in FIG. 7C, each of the multiple first through holes 261 is filled with a powdery first thermoelectric member 52. Each of the multiple second through holes 262 is filled with a powdery second thermoelectric member 53.

Figure 7D:
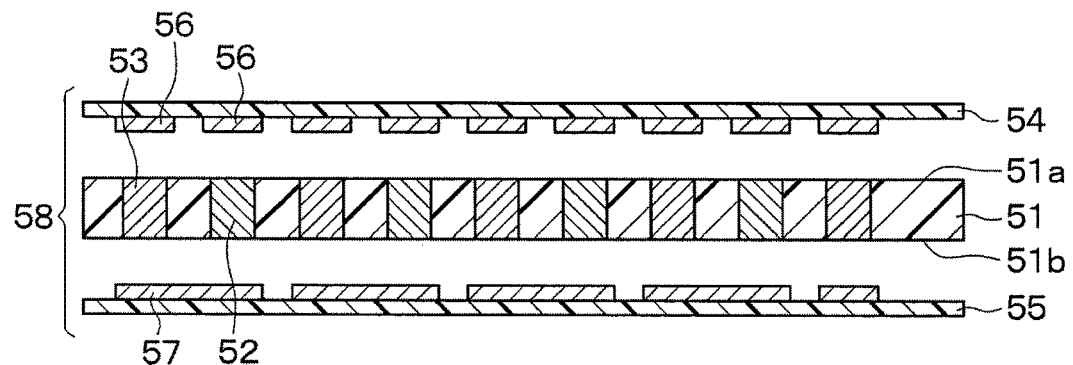
FIG. 7D is a cross-sectional view showing a process for manufacturing the heat flux sensor subsequent to FIG. 7C.

Subsequently, as shown in FIG. 7D, a first protective member 54 and a second protective member 55 are prepared. Multiple first conductor patterns 56 are formed on a surface of the first protective member 54. Multiple second conductor patterns 57 are formed on a surface of the second protective member 55.

Then, the first protective member 54 is stacked on the first surface 51a of the base material 51 such that the surface of the first protective member 54 on which the first conductor patterns 56 are formed faces the base material 51. The second protective member 55 is stacked on the second surface 51b of the base material 51 such that the surface of the second protective member 55 on which the second conductor patterns 57 are formed faces the base material 51. As a result, a stacked body 58 in which the base material 51, the first protective member 54, and the second protective member 55 are stacked is formed.

Figure 7E:
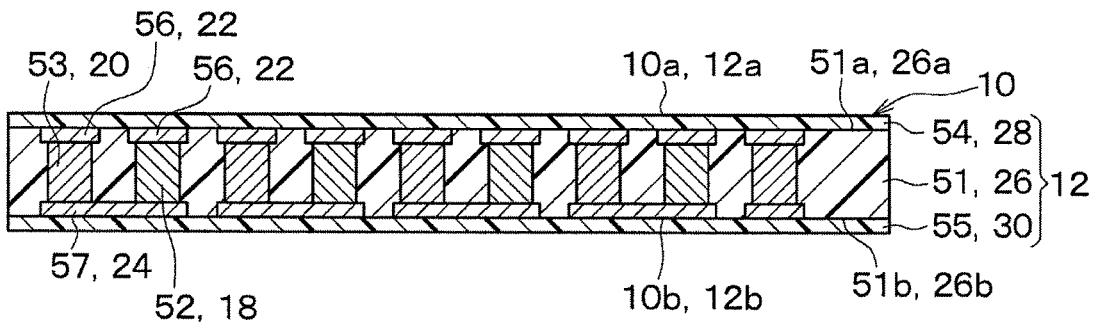
FIG. 7E is a cross-sectional view showing a process for manufacturing the heat flux sensor subsequent to FIG. 7D.

Subsequently, as shown in FIG. 7E, the stacked body 58 is pressurized while being heated. As a result, the base material 51, the first protective member 54, and the second protective member 55 are integrated together. Each of the multiple first thermoelectric members 52 is sintered. Each of the multiple second thermoelectric members 53 is sintered. In this manner, the insulation member 12 in which the multiple first thermoelectric members 18, the multiple second thermoelectric members 20, the multiple first conductor patterns 22, and the multiple second conductor patterns 24 are internally disposed is formed. In other words, the sensor main body portion 10 is formed. The insulation member 12 has the first surface 12a and the second surface 12b.

The base material 51, the first surface 51a, the second surface 51b, the first thermoelectric member 52, the second thermoelectric member 53, the first protective member 54, the second protective member 55, the first conductor pattern 56, and the second conductor pattern 57 correspond to the base material 26, the first surface 26a, the second surface 26b, the first thermoelectric member 18, the second thermoelectric member 20, the first protective member 28, the second protective member 30, the first conductor pattern 22, and the second conductor pattern 24, respectively.

Figure 7F:
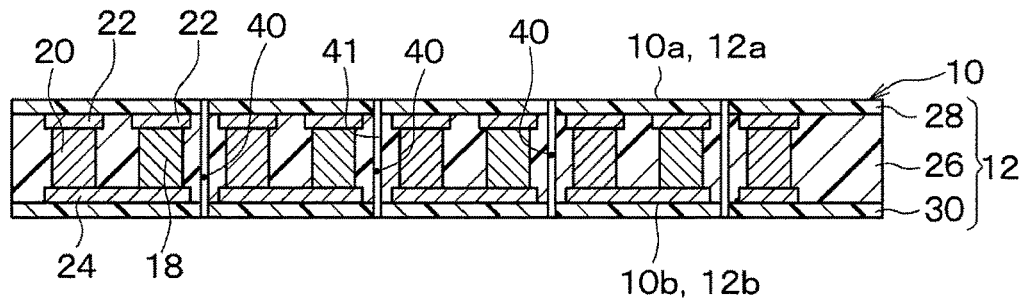
FIG. 7F is a cross-sectional view showing a process for manufacturing the heat flux sensor subsequent to FIG. 7E.

Subsequently, as shown in FIG. 7F, the multiple through holes 40 are formed in the insulation member 12. In other words, multiple cylindrical inner wall surfaces 41 are formed in the insulation member 12.

Figure 7G:
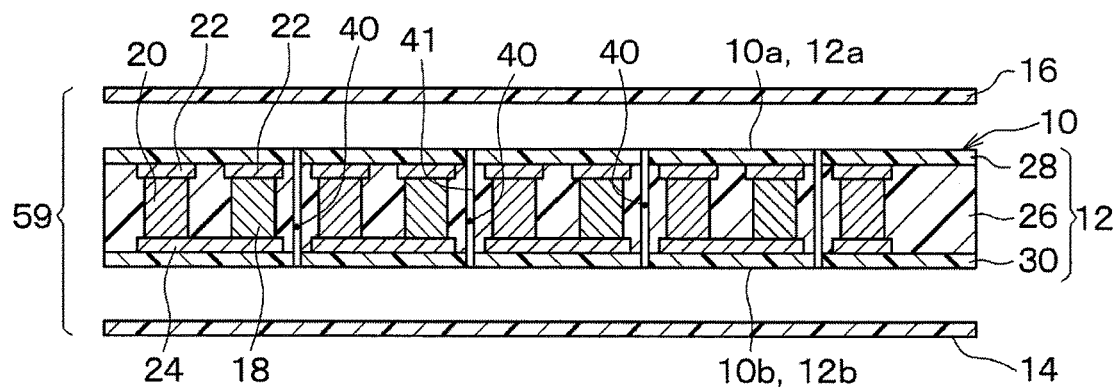
FIG. 7G is a cross-sectional view showing a process for manufacturing the heat flux sensor subsequent to FIG. 7F.

Subsequently, as shown in FIG. 7G, the first moisture absorbing member 14 and the second moisture absorbing member 16 are prepared. The second moisture absorbing member 16 is stacked on the first surface 12a of the insulation member 12. The first moisture absorbing member 14 is stacked on the second surface 12b of the insulation member 12. As a result, a stacked body 59 in which the insulation member 12, the first moisture absorbing member 14, and the second moisture absorbing member 16 are stacked on each other is formed.

Figure 7H:
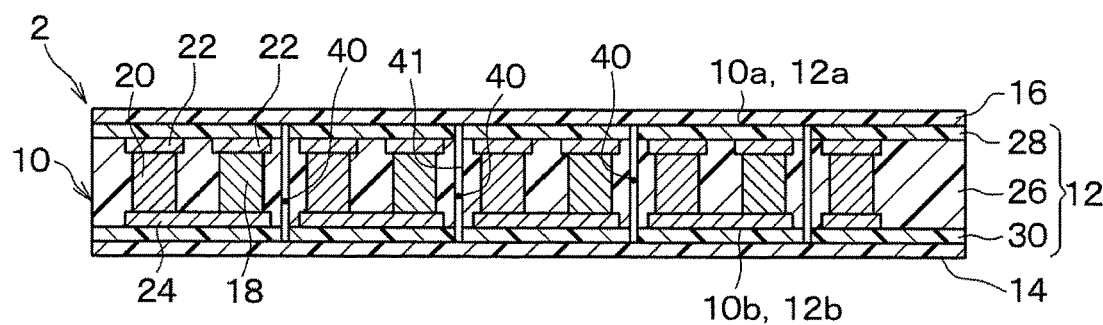
FIG. 7H is a cross-sectional view showing a process for manufacturing the heat flux sensor subsequent to FIG. 7G.

Subsequently, as shown in FIG. 7H, the stacked body 59 is pressurized. Alternatively, the stacked body 59 is pressurized while being heated. As a result, the insulation member 12, the first moisture absorbing member 14, and the second moisture absorbing member 16 are integrated together. In this manner, the heat flux sensor 2 of the present embodiment is manufactured.

Next, the measurement of the physiological heat quantity by the measuring instrument 1 of the present embodiment will be described.

Figure 8:
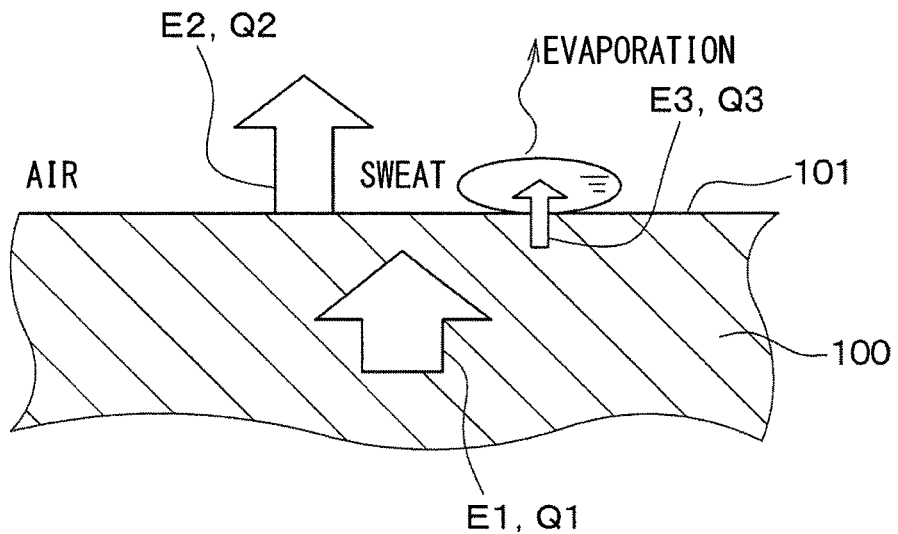
FIG. 8 is a conceptual diagram showing a flow of thermal energy discharged from an inside to an outside of the human body.

A thermal energy E1 discharged from the inside of the human body 100 to the outside flows as shown in FIG. 8. That is, a part E2 of the thermal energy E1 from the human body 100 is convectively discharged from the surface 101 of the human body 100 to the air. Another part E3 of the thermal energy E1 from the human body 100 is used as a latent heat of evaporation when sweat existing on the surface 101 of the human body 100 evaporates.

Therefore, a physiological heat quantity Q1 discharged from the inside to the outside of the human body 100 is a sum total of a heat quantity Q2 of the convection component and a heat quantity Q3 of the latent heat of evaporation. The physiological heat quantity Q1 corresponds to the amount of thermal energy E1. The heat quantity Q2 of the convection component corresponds to the amount of thermal energy E2. The heat quantity Q3 of the latent heat of evaporation corresponds to the amount of thermal energy E3.

Unlike the present embodiment, in a case where the heat flux sensor does not have air permeability, sweat generated on the surface of the human body cannot pass through the heat flux sensor. The sweat generated on the surface of the human body does not evaporate, but accumulates between the surface of the human body and the heat flux sensor. For that reason, the user feels uncomfortable. In addition, since evaporation is not conducted, a flow of thermal energy passing through the heat flux sensor from the surface of the human body is different from the actual state described above. Therefore, when a heat flux sensor having no air permeability is used, the physiological heat quantity emitted from the human body cannot be accurately measured.

Figure 9:
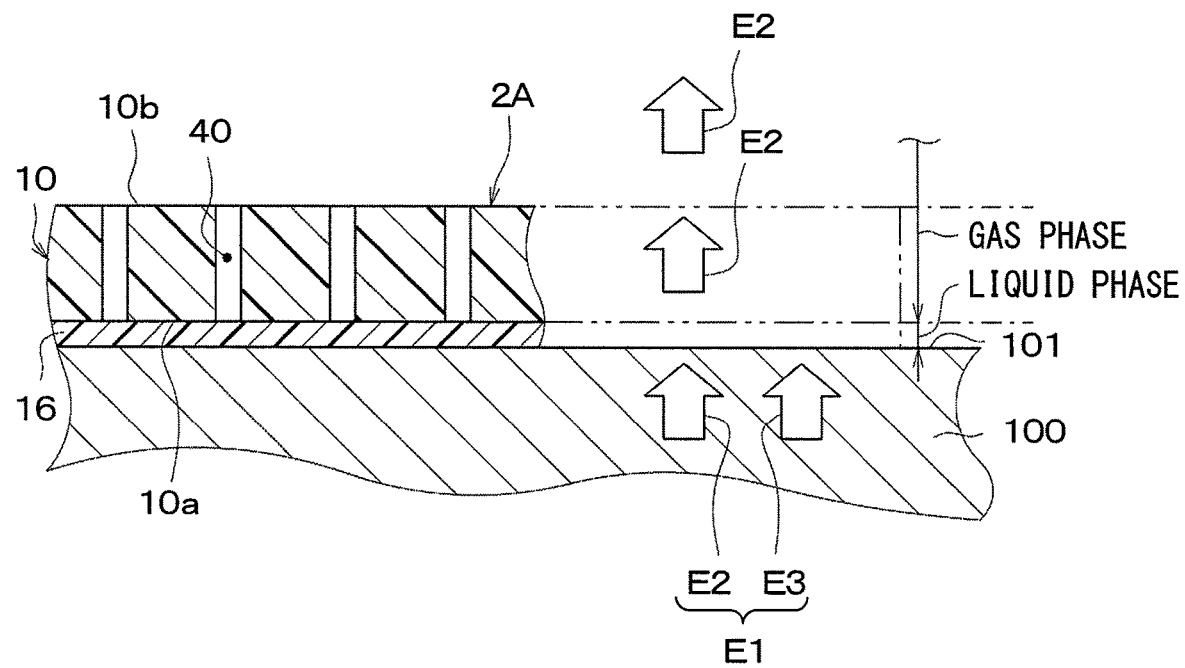
FIG. 9 is a cross-sectional view of a heat flux sensor as a comparative example 1, which shows a state in which the heat flux sensor is attached to a surface of a human body.

FIG. 9 shows a heat flux sensor 2A as a comparative example 1. The heat flux sensor 2A of the comparative example 1 is different from the heat flux sensor 2 of the present embodiment in that the first moisture absorbing member 14 is not provided. The other configuration of the heat flux sensor 2A of the comparative example 1 is the same as that of the heat flux sensor 2 of the present embodiment.

As shown in FIG. 9, when the heat flux sensor 2 A of the comparative example 1 is attached to the surface 101 of the human body 100, the sweat generated on the surface 101 of the human body 100 is absorbed by the second moisture absorbing member 16. The sweat evaporates inside the second moisture absorbing member 16. The evaporated sweat passes through each of the multiple through holes 40 and is discharged into the air. At this time, thermal energy is used as latent heat of evaporation on the side of the sensor main body portion 10 adjacent to the human body 100.

For that reason, of the thermal energy E1 emitted from the human body 100, the thermal energy E3 corresponding to the latent heat of evaporation does not pass through the sensor main body portion 10. Of the thermal energy E1 emitted from the human body 100, only the thermal energy E2 of the convection component passes through the sensor main body portion 10. As described above, a flow of the thermal energy passing through the heat flux sensor 2A of the comparative example 1 is different from the actual state described above. Therefore, when the heat flux sensor 2A of the comparative example 1 is used alone, it is difficult to accurately measure the physiological heat quantity emitted from the human body.

On the other hand, as shown in FIG. 3, when the heat flux sensor 2 of the present embodiment is attached to the surface 101 of the human body 100, the sweat generated on the surface 101 of the human body 100 is absorbed by the second moisture absorbing member 16. The sweat absorbed by the second moisture absorbing member 16 moves toward the second surface 10b through each of the multiple through holes 40 by a surface tension. The sweat that has moved toward the second surface 10b is absorbed by the first moisture absorbing member 14. Thereafter, the sweat evaporates inside the first moisture absorbing member 14. The evaporated sweat is discharged from the first moisture absorbing member 14 into the air.

In the heat flux sensor 2A of the comparative example 1, the second surface 10b of the sensor main body portion 10 is not covered with the moisture absorbing member. The multiple through holes 40 are opened to air around the heat flux sensor 2A. For that reason, the sweat generated on the surface 101 of the human body 100 evaporates before passing through the multiple through holes 40. Therefore, as shown in FIG. 9, sweat is in a liquid phase on the human body side of the first surface 10a of the sensor main body portion 10. The sweat is in the gas phase on the anti-human body side of the first surface 10a of the sensor main body portion 10.

On the other hand, in the heat flux sensor 2 of the present embodiment, the second surface 10b of the sensor main body portion 10 and the multiple through holes 40 are covered with the first moisture absorbing member 14. The multiple through holes 40 are nearly in a closed state. In a state in which the first moisture absorbing member 14 absorbs sweat, the multiple through holes 40 are closed by the first moisture absorbing member 14. For that reason, in the heat flux sensor 2 of the present embodiment, the sweat generated on the surface 101 of the human body 100 evaporates on the second surface 10b side after passing through the multiple through holes 40. Therefore, as shown in FIG. 3, the sweat is in a liquid phase inside the heat flux sensor 2. The sweat is in a gas phase on the side of the heat flux sensor 2 opposite to the human body 100.

As described above, when the heat flux sensor 2 of the present embodiment is used, the sweat on the surface 101 of the human body 100 is absorbed by the second moisture absorbing member 16, and then suctioned up to the first moisture absorbing member 14 through the multiple through holes 40. Thereafter, the sweat evaporates on the second surface 10b side of the sensor main body portion 10. At this time, thermal energy is used as latent heat of evaporation on the second surface 10b side of the sensor main body portion 10. For that reason, as shown in FIG. 3, both the thermal energy E2 of the convection component and the thermal energy E3 of the latent heat of evaporation component pass through the sensor main body portion 10. In this manner, a flow of thermal energy passing through the heat flux sensor 2 is the same as the actual situation described above.

For that reason, the sensor main body portion 10 can output a sensor signal corresponding to the sum total of the heat quantity Q2 for the convection and the heat quantity Q3 for the latent heat of evaporation. For that reason, with the use of the heat flux sensor 2 according to the present embodiment, the physiological heat quantity Q1 emitted from the human body 100 can be accurately measured.

As described above, according to the heat flux sensor 2 of the present embodiment, the sweat generated on the surface 101 of the human body 100 can be moved to the second surface 10b of the sensor main body portion 10 through the multiple through holes 40. Therefore, the user can be inhibited from feeling uncomfortable due to sweat.

Further, according to the heat flux sensor 2 of the present embodiment, the multiple through holes 40 and the first moisture absorbing member 14 are provided. As a result, the sweat can be evaporated on the second surface 10b side of the sensor main body portion 10. For that reason, as shown in FIG. 3, both of the thermal energy E2 of the convection component and the thermal energy E3 of the latent heat of evaporation component are allowed to pass through the sensor main body portion 10. Therefore, with the use of the heat flux sensor 2 according to the present embodiment, the heat quantities Q2 and Q3 used for both convection and latent heat of evaporation can be measured. Therefore, according to the measuring instrument 1 of the present embodiment, the physiological heat quantity Q1 emitted from the human body 100 can be accurately measured.

In addition, according to the heat flux sensor 2 of the present embodiment, it is less likely that the user will feel uncomfortable due to the sweat by the second moisture absorbing member 16. Further, the second moisture absorbing member 16 can facilitate the movement of sweat to each of the multiple through holes 40.

Second Embodiment

Figure 10:
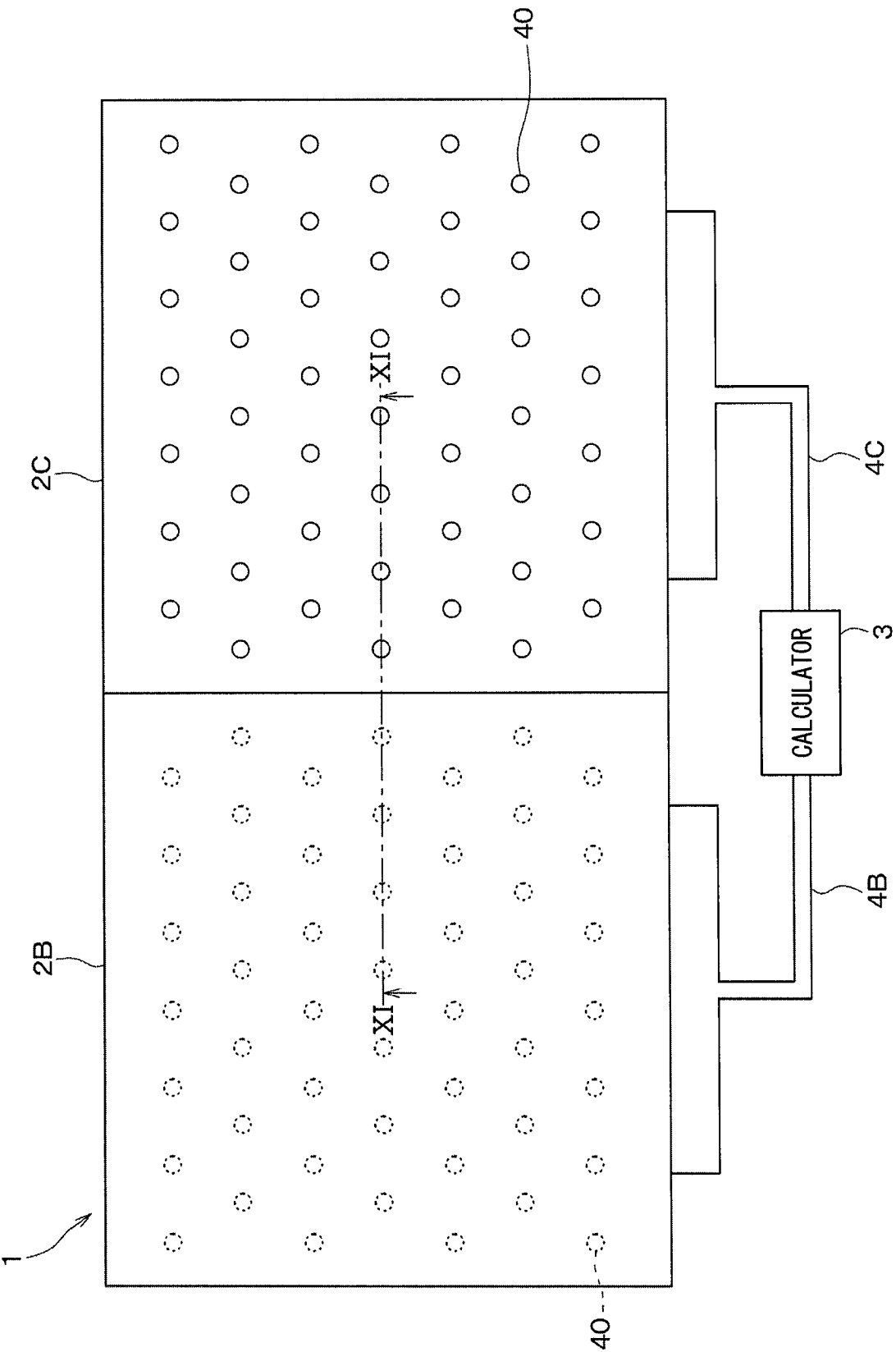
FIG. 10 is a diagram showing an overall configuration of a measuring instrument for a physiological heat quantity according to a second embodiment.
Figure 11:
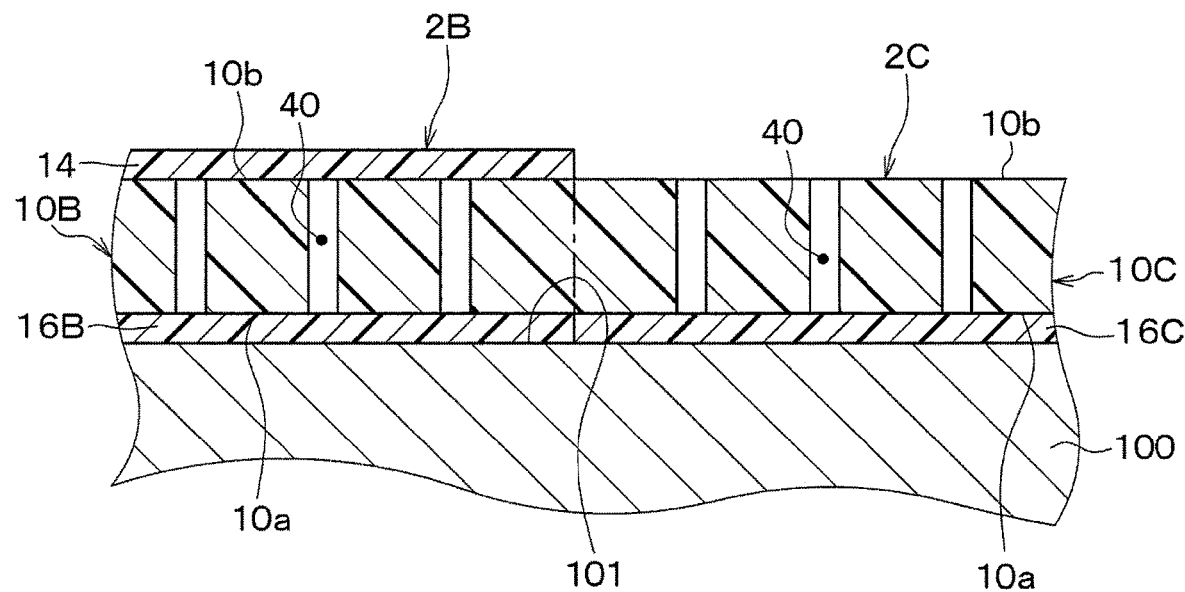
FIG. 11 is a cross-sectional view taken along a line XI-XI of the heat flux sensor shown in FIG. 10.

As shown in FIGS. 10 and 11, a measuring instrument 1 according to the present embodiment is different from the measuring instrument 1 of the first embodiment in that the measuring instrument 1 includes two heat flux sensors 2B and 2C.

The measuring instrument 1 includes a first heat flux sensor 2B, a second heat flux sensor 2C, and a calculator 3. The first heat flux sensor 2B and the second heat flux sensor 2C are both attached to the surface of the human body. The first heat flux sensor 2B and the second heat flux sensor 2C each detect a heat flux emitted from the human body. The first heat flux sensor 2B and the second heat flux sensor 2C are each in a film-shape. A planar shape of each of the first heat flux sensor 2B and the second heat flux sensor 2C is a square.

The first heat flux sensor 2B has the same structure as that of the heat flux sensor 2 in the first embodiment shown in FIG. 2. The first heat flux sensor 2B includes a first sensor main body portion 10B, a first moisture absorbing member 14, and a second moisture absorbing member 16B. The first sensor main body portion 10B, the first moisture absorbing member 14, and the second moisture absorbing member 16B are respectively the same as the sensor main body portion 10, the first moisture absorbing member 14, and the second moisture absorbing member 16 of the first embodiment. Multiple through holes 40 are formed in the first sensor main body portion 10B. The first sensor main body portion 10B outputs a first sensor signal to the calculator 3.

The second heat flux sensor 2C has the same structure as that of the heat flux sensor 2A of the comparative example 1 shown in FIG. 9. The second heat flux sensor 2C includes a second sensor main body portion 10C and a third moisture absorbing member 16C. The second sensor main body portion 10C is the same as the sensor main body portion 10 of the heat flux sensor 2 in the first embodiment. The third moisture absorbing member 16C is the same as the second moisture absorbing member 16 of the heat flux sensor 2 in the first embodiment.

The second sensor main body portion 10 C is attached to the human body such that a first surface 10a is adjacent to the human body. The second sensor main body portion 10C outputs a sensor signal according to the heat flux passing through the second sensor main body portion 10 C from the first surface 10a toward the second surface 10b.

Multiple through holes 40 are formed in the second sensor main body portion 10C. The second surface 10b of the second sensor main body portion 10C is not covered with the moisture absorbing member. For that reason, a region of the second surface 10b of the second sensor main body portion 10C in which the multiple through holes 40 are formed is exposed to an external space. In the present embodiment, an entire area of the second surface 10b of the second sensor main body portion 10C is exposed to the external space.

The second sensor main body portion 10C is formed of an integrally molded article integrally molded with the first sensor main body portion 10B. In other words, the second sensor main body portion 10C is formed seamlessly with the first sensor main body portion 10B. More specifically, the insulation member 12 of the second sensor main body portion 10C is formed of an integrally molded article integrally molded with the insulation member 12 of the first sensor main body portion 10B. As a result, the first heat flux sensor 2B and the second heat flux sensor 2C are integral. For that reason, the number of components of the measuring instrument 1 can be reduced as compared with the case where the first heat flux sensor 2B and the second heat flux sensor 2C are configured separately. However, the first heat flux sensor 2B and the second heat flux sensor 2C may be formed separately.

The third moisture absorbing member 16C is a member separate from the second moisture absorbing member 16B. However, the third moisture absorbing member 16C may be formed of an integrally molded product integrally molded with the second moisture absorbing member 16B.

The first heat flux sensor 2B and the second heat flux sensor 2C are manufactured through the same manufacturing process as will be described below. The processes shown in FIGS. 7A to 7F described in the first embodiment is performed. As a result, the first sensor main body portion 10B and the second sensor main body portion 10C are manufactured.

Thereafter, as in the process shown in FIG. 7G, the first moisture absorbing member 14 and the second moisture absorbing member 16B are stacked on the first sensor main body portion 10B. On the other hand, the third moisture absorbing member 16C is stacked on the second sensor main body portion 10C. As a result, a stacked body is formed.

Thereafter, the stacked body is pressurized. Alternatively, the stacked body is pressurized while being heated. As a result, the first heat flux sensor 2B and the second heat flux sensor 2C are manufactured.

The calculator 3 is connected to the first sensor main body portion 10 B of the first heat flux sensor 2B through the wiring 4B. The calculator 3 is connected to the second sensor main body portion 10C of the second heat flux sensor 2C through the wiring 4C.

Similarly to the first embodiment, the calculator 3 calculates the physiological heat quantity emitted from the human body based on the first sensor signal. Further, the calculator 3 calculates the amount of perspiration of the human body based on the first sensor signal and a second sensor signal. At this time, the calculator 3 uses a relationship between a difference between the heat quantities passing through the first sensor main body portion 10B and the second sensor main body portion 10C and the amount of perspiration of the human body.

As shown in FIG. 11, the first heat flux sensor 2B and the second heat flux sensor 2C are attached to the surface 101 of the human body 100. In this case, as described in the first embodiment, in the first heat flux sensor 2B, as shown in FIG. 3, both of the thermal energy E2 of the convection component and the thermal energy E3 of the evaporation latent heat component pass through the sensor main body portion 10. For that reason, the first sensor main body portion 10B can output a first sensor signal corresponding to the sum total of the heat quantity Q2 of the convection component and the heat quantity Q3 of the latent heat of evaporation.

On the other hand, in the second heat flux sensor 2C, as described in the heat flux sensor 2 A of the comparative example 1 relative to the first embodiment, as shown in FIG. 9, the thermal energy E2 of the convection component passes through the second sensor main body portion 10C, and the thermal energy E3 of the evaporation latent heat component does not pass through the second sensor main body portion 10C. For that reason, the second sensor main body portion 10C can output the second sensor signal corresponding only to the heat quantity Q2 of the convection component out of the heat quantity Q2 of the convection component and the heat quantity Q3 of the evaporation latent heat component.

Therefore, the calculator 3 calculates the physiological heat quantity Q1 based on the first sensor signal. The calculator 3 calculates the heat quantity Q2 for the convection based on the second sensor signal. The calculator 3 calculates the heat quantity Q3 of the latent heat of evaporation according to a difference between the physiological heat quantity Q1 and the heat quantity Q2 of the convection component. The amount of perspiration is calculated according to the calculated heat quantity Q3 of the latent heat of evaporation. In the calculation of the amount of perspiration, the calculator 3 uses a predetermined relationship between the heat quantity Q3 of the latent heat of evaporation and the amount of perspiration. This relationship represents a relationship between a difference in the heat quantities passing through the first sensor main body portion 10B and the second sensor main body portion 10C and the amount of perspiration of the human body.

In this manner, according to the measuring instrument 1 of the present embodiment, in addition to measuring the physiological heat quantity Q1, the amount of perspiration of the human body can be measured.

According to the present embodiment, the calculator 3 calculates the heat quantity Q3 of the latent heat of evaporation according to the difference between the physiological heat quantity Q1 and the heat quantity Q2 of the convection portion, but the heat quantity Q3 of the latent heat of evaporation may be directly calculated according to the first sensor signal and the second sensor signal. According to the present embodiment, the calculator 3 calculates the amount of perspiration according to the heat quantity Q3 of the evaporation latent heat, but the amount of perspiration may be directly calculated according to the first sensor signal and the second sensor signal. Also in the calculation of the sweat amount in this case, the relationship between the difference in the heat quantities passing through the first sensor main body portion 10B and the second sensor main body portion 10C and the amount of perspiration of the human body is used.

In the present embodiment, the first sensor signal and the second sensor signal are separately input to the calculator 3, but the present disclosure is not limited to the above configuration. When the calculator 3 calculates the amount of perspiration, the difference between the first sensor signal and the second sensor signal may be directly input to the calculator 3.

Third Embodiment

Figure 12:
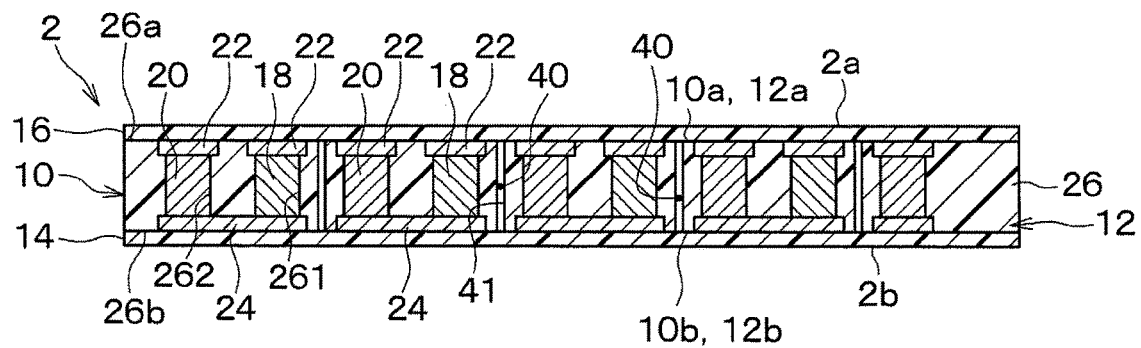
FIG. 12 is a cross-sectional view of a heat flux sensor according to a third embodiment.

As shown in FIG. 12, the present embodiment is different from the first embodiment in a configuration of a sensor main body portion 10 of a heat flux sensor 2. The other configuration is the same as that of the first embodiment. FIG. 12 corresponds to FIG. 6.

An insulation member 12 is made of a film-shaped base material 26. A first surface 26a of the base material 26 configures the first surface 12a of the insulation member 12. A second surface 26b of the base material 26 configures the second surface 12b of the insulation member 12.

Multiple first thermoelectric members 18 are disposed in multiple first through holes 261. Multiple second thermoelectric members 20 are disposed in multiple second through holes 262. Multiple first conductor patterns 22 are disposed on the first surface 26a of the base material 26. Multiple second conductor patterns 24 are disposed on the second surface 26b of the base material 26.

In this way, the multiple first thermoelectric members 18 and the multiple second thermoelectric members 20 are disposed inside the insulation member 12. The multiple first conductor patterns 22 and the multiple second conductor patterns 24 are exposed from the insulation member 12.

Similarly to the first embodiment, multiple through holes 40 are formed in the insulation member 12. Each of the multiple through holes 40 is defined by an inner wall surface 41.

Figure 13A:
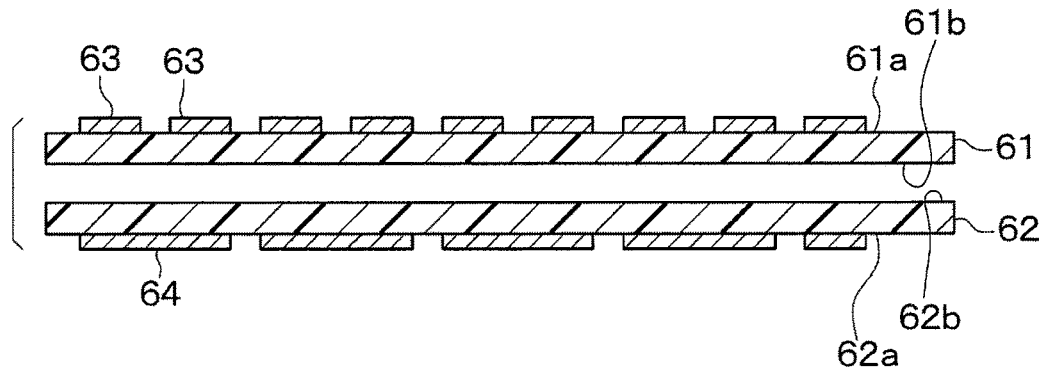
FIG. 13A is a cross-sectional view showing a process for manufacturing a heat flux sensor according to the third embodiment.
Figure 13B:
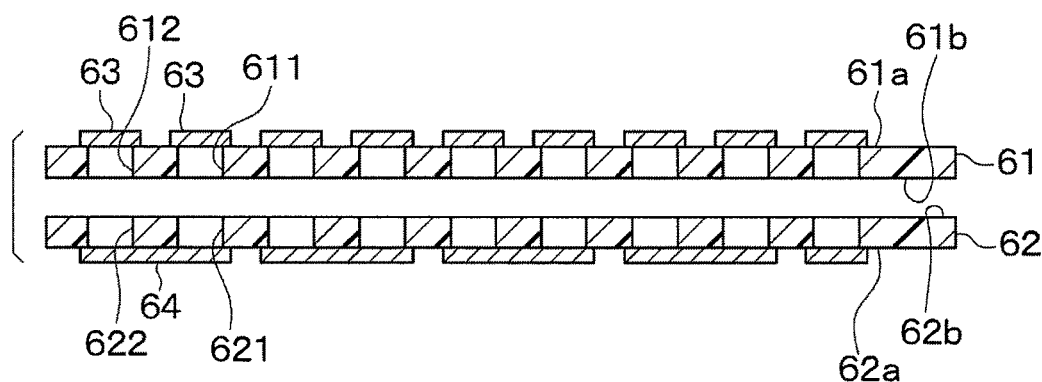
FIG. 13B is a cross-sectional view showing a process for manufacturing the heat flux sensor subsequent to FIG. 13A.

Next, a method of manufacturing the heat flux sensor 2 according to the present embodiment will be described with reference to FIGS. 13A to 13G. In FIGS. 13A and 13B, a first base material member 61 and a second base material member 62 are shown side by side in a state before stacking.

As shown in FIG. 13A, the film-shaped first base material member 61 and the film-shaped second base material member 62 are prepared. The first base material member 61 has a first surface 61a and a second surface 61b on a side opposite to the first surface 61a. Multiple first conductor patterns 63 are formed on the first surface 61a of the first base material member 61. The second base material member 62 has a first surface 62a and a second surface 62b on a side opposite to the first surface 62a. Multiple second conductor patterns 64 are formed on the first surface 62a of the second base material member 62.

Subsequently, as shown in FIG. 13B, multiple first through holes 611 and multiple second through holes 612 are formed in the first base material member 61. The multiple first through holes 611 and the multiple second through holes 612 penetrate through the first base material member 61 from the first surface 61a to the second surface 61b. The first through holes 611 and the second through holes 612 are alternately disposed. The first conductor pattern 63 forms bottoms of the multiple first through holes 611 and the multiple second through holes 612.

Similarly, multiple first through holes 621 and multiple second through holes 622 are formed in the second base material member 62. The multiple first through holes 621 and the multiple second through holes 622 penetrate through the second base material member 62 from the first surface 62a to the second surface 62b. The first through holes 621 and the second through holes 622 are alternately disposed. The second conductor pattern 64 forms bottoms of the multiple first through holes 621 and the multiple second through holes 622.

Figure 13C:
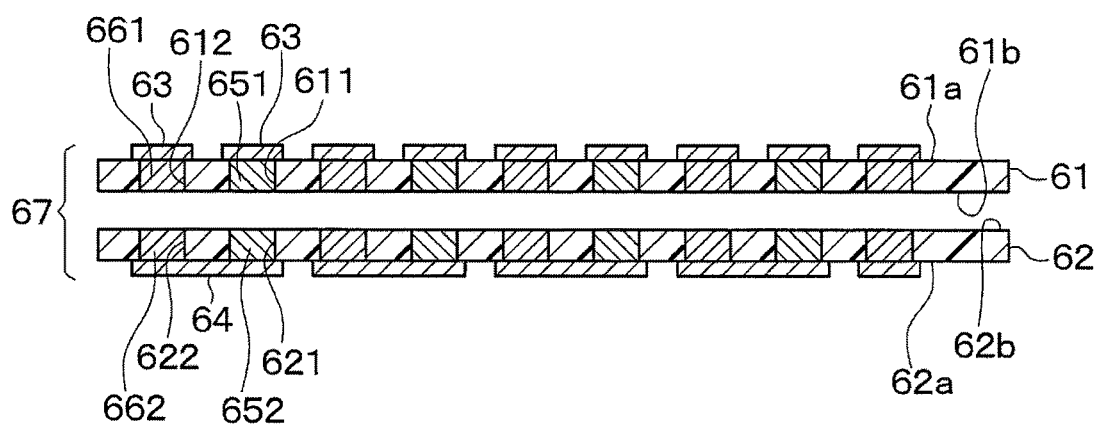
FIG. 13C is a cross-sectional view showing a process for manufacturing the heat flux sensor subsequent to FIG. 13B.

Subsequently, as shown in FIG. 13C, in the first base material member 61, each of the multiple first through holes 611 is filled with a powdery first thermoelectric member 651. Each of the multiple second through holes 612 is filled with a powdery second thermoelectric member 661.

Similarly, in the second base material member 62, each of the multiple first through holes 621 is filled with a powdery first thermoelectric member 652. Each of the multiple second through holes 622 is filled with a powdery second thermoelectric member 662.

Subsequently, a stacked body 67 in which the first base material member 61 and the second base material portion 62 are laminated is formed. At this time, the second surface 61b of the first base material member 61 and the second surface 62b of the second base material member 62 face each other. The first thermoelectric member 651 of the first base material member portion 61 and the first thermoelectric member 652 of the second base material member portion 62 face each other. The second thermoelectric member 661 of the first base material member portion 61 and the first thermoelectric member 662 of the second base material member portion 62 face each other.

Subsequently, the stacked body 67 is pressurized while being heated. As a result, the first base material member 61 and the second base material member 62 are integrated together. Each of the multiple first thermoelectric members 651 and 652 is sintered. Each of the multiple second thermoelectric members 661 and 662 is sintered.

Figure 13D:
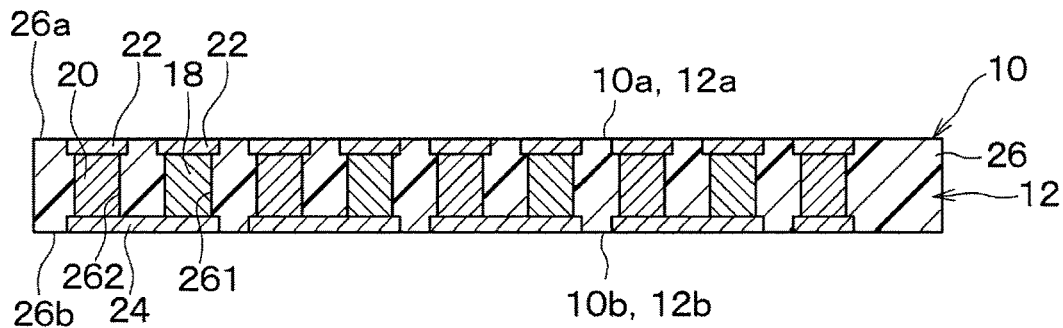
FIG. 13D is a cross-sectional view showing a process for manufacturing the heat flux sensor subsequent to FIG. 13C.

In this manner, as shown in FIG. 13D, the insulation member 12 in which the multiple first thermoelectric members 18 and the multiple second thermoelectric members 20 are disposed is formed. In other words, the sensor main body portion 10 is formed. The insulation member 12 has a first surface 12a and a second surface 12b.

The first base material member 61 and the second base material member 62 correspond to the base material member 26. The first surface 61a of the first base material member 61 corresponds to the first surface 12a of the insulation member 12. The first surface 62a of the second base material member 62 corresponds to the second surface 12b of the insulation member 12. The first through holes 611 of the first base material member 61 and the first through holes 621 of the second base material member 62 correspond to the first through holes 261 of the base material member 26. The second through holes 612 of the first base material member portion 61 and the second through holes 622 of the second base material member portion 62 correspond to the second through holes 262 of the base material member 26. The first conductor pattern 63 and the second conductor pattern 64 correspond to the first conductor pattern 22 and the second conductor pattern 24, respectively.

Figure 13E:
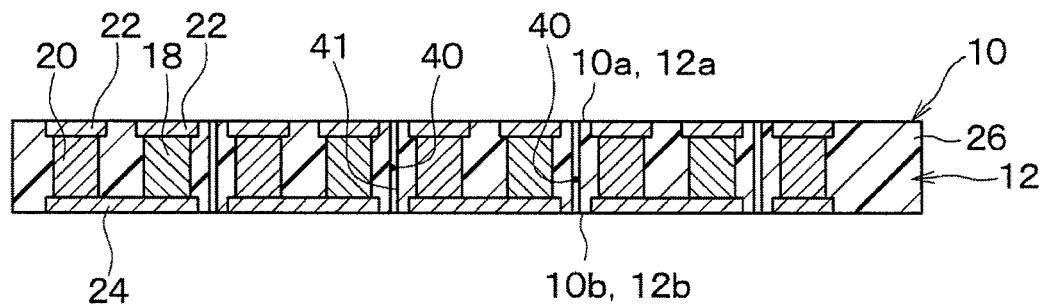
FIG. 13E is a cross-sectional view showing a process for manufacturing the heat flux sensor subsequent to FIG. 13D.

Subsequently, as shown in FIG. 13E, multiple through holes 40 are formed in the insulation member 12.

Figure 13F:
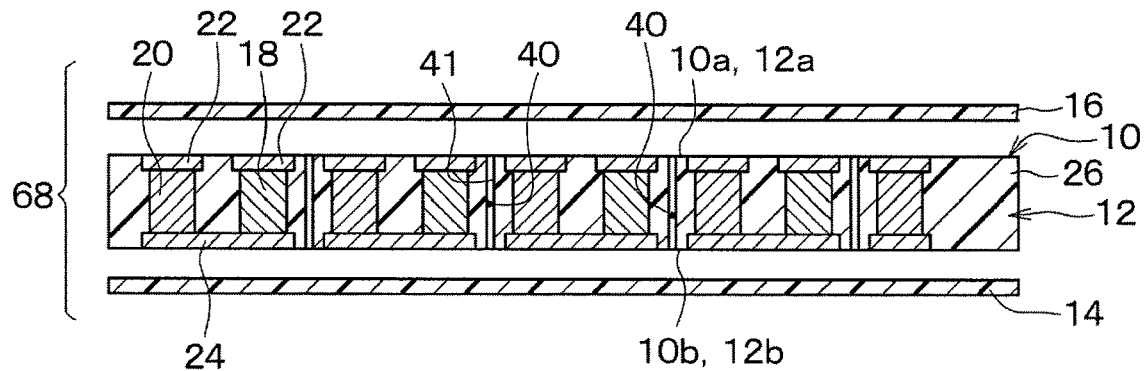
FIG. 13F is a cross-sectional view showing a process for manufacturing the heat flux sensor subsequent to FIG. 13E.

Subsequently, as shown in FIG. 13F, the first moisture absorbing member 14 and the second moisture absorbing member 16 are prepared. The second moisture absorbing member 16 is stacked on the first surface 12a of the insulation member 12. The first moisture absorbing member 14 is stacked on the second surface 12b of the insulation member 12. As a result, a stacked body 68 in which the insulation member 12, the first moisture absorbing member 14, and the second moisture absorbing member 16 are stacked is formed.

Figure 13G:
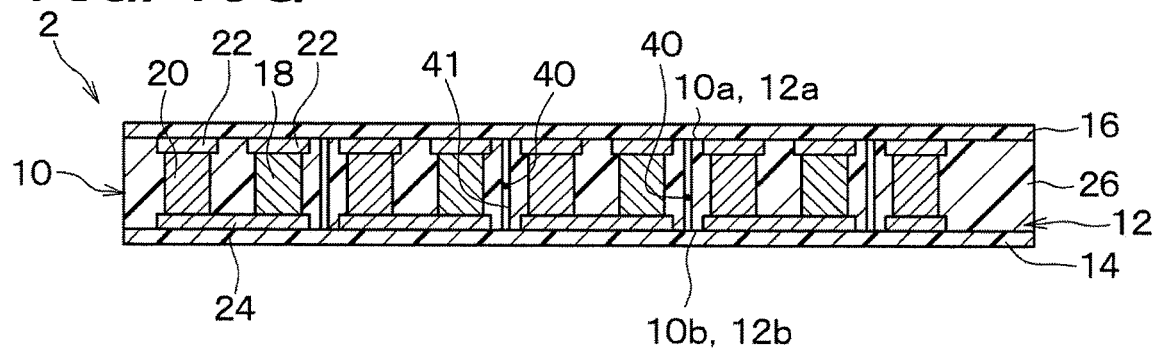
FIG. 13G is a cross-sectional view showing a process for manufacturing the heat flux sensor subsequent to FIG. 13F.

Subsequently, as shown in FIG. 13G, the stacked body 68 is pressurized. Alternatively, the stacked body 68 is pressurized while being heated. As a result, the insulation member 12, the first moisture absorbing member 14, and the second moisture absorbing member 16 are integrated together. In this manner, the heat flux sensor 2 of the present embodiment is manufactured.

Even when the heat flux sensor 2 of the present embodiment is used, the similar effects to those of the first embodiment can be achieved. The first sensor main body portion 10B of the first heat flux sensor 2B and the second sensor main body portion 10C of the second heat flux sensor 2 C according to the second embodiment may have the same configuration as the sensor main body portion 10 of the present embodiment.

Other Embodiments (1) In each of the embodiments described above, the shape of each of the multiple through holes 40 in the first surface 10a and the second surface 10b of the sensor main body portion 10 is circular, but may be other shapes such as polygonal or linear.

(2) In the first embodiment, the heat flux sensor 2 includes the second moisture absorbing member 16, but may not include the second moisture absorbing member 16. Even in this case, the sweat can move between the sensor main body portion 10 and the surface of the human body. For that reason, the similar effects to those of the first embodiment can be achieved. Similarly, in the second embodiment, each of the first heat flux sensor 2B and the second heat flux sensor 2C includes the second moisture absorbing member 16B and the third moisture absorbing member 16C, but may not include the second moisture absorbing member 16B and the third moisture absorbing member 16C. Even in this case, the similar effects to those of the second embodiment can be achieved.

(3) In the first embodiment, the planar shape of the heat flux sensor 2 is a quadrangle, but may be another shape such as a circle. Similarly, in the second embodiment, the planar shapes of the first heat flux sensor 2B and the second heat flux sensor 2C are square, but may be other shapes such as a circle.

(4) The configuration of the sensor main body portion 10 of the heat flux sensor 2 is not limited to the first embodiment and the third embodiment. The configuration of the sensor main body portion 10 may be other than the first embodiment and the third embodiment. The sensor main body portion 10 may output a sensor signal corresponding to the heat flux passing through the sensor main body portion 10 from the first surface 10a toward the second surface 10b.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

According to a first aspect shown in part or all of the embodiments described above, the measuring instrument of the physiological heat quantity includes a heat flux sensor and a calculator. The heat flux sensor includes a film-shaped sensor main body portion and a film-shaped moisture absorbing member capable of absorbing sweat and releasing the absorbed sweat. The sensor main body portion has a first surface and a second surface on the opposite side of the first surface. The sensor main body portion is formed with multiple through holes that penetrate through the sensor main body portion from the first surface to the second surface. The sensor main body portion has the first surface on a side that is adjacent to the human body when in use, and outputs a sensor signal corresponding to a heat flux passing through the sensor main body portion from the first surface toward the second surface. The moisture absorbing member is stacked on the second surface of the sensor main body portion. The calculator calculates the physiological heat quantity emitted from the human body based on the sensor signal.

According to a second aspect, the moisture absorbing member is a first moisture absorbing member. The heat flux sensor has a film-shaped second moisture absorbing member capable of absorbing sweat and releasing the absorbed sweat. The second moisture absorbing member is stacked on the first surface of the sensor main body portion, and is disposed between the surface of the human body and the sensor main body portion in a state in which the heat flux sensor is attached to the surface of the human body.

According to the above configuration, it is less likely that a person to be measured will feel uncomfortable due to sweat, since the second moisture absorbing member is provided. Further, the second moisture absorbing member can facilitate the movement of sweat to each of the multiple through holes.

According to a third aspect, the sensor main body portion includes the insulation member, the multiple first thermoelectric members, the multiple second thermoelectric members, the multiple first conductor patterns, and the multiple second conductor patterns. The insulation member is in the form of a film having a first surface and a second surface on the opposite side of the first surface, and is flexible. The multiple first thermoelectric members are disposed inside the insulation member and are made of a first thermoelectric material. The multiple second thermoelectric members are disposed inside the insulation member, are made of a second thermoelectric material different from the first thermoelectric material. The multiple first thermoelectric members and the multiple first thermoelectric members are alternately arranged in the insulation member. The multiple first conductor patterns are disposed on the first surface side with respect to the multiple first thermoelectric members and the multiple second thermoelectric members. Each of the first conductor patterns connects the first thermoelectric member and the second thermoelectric member disposed adjacent to each other, among the multiple first thermoelectric members and the multiple second thermoelectric members. The multiple second conductor patterns are disposed on the second surface side with respect to the multiple first thermoelectric members and the multiple second thermoelectric members. Each of the second conductor patterns connects the first thermoelectric member and the second thermoelectric member disposed adjacent to each other, among the multiple first thermoelectric members and the multiple second thermoelectric members. The first surface of the insulation member configures the first surface of the sensor main body portion. The second surface of the insulation member configures the second surface of the sensor main body portion. The multiple through holes are each located in a region of the insulation member where the first thermoelectric member, the second thermoelectric member, the first conductor pattern, and the second conductor pattern are not disposed.

As a specific configuration of the sensor main body portion, such a configuration can be adopted.

According to a fourth aspect, the heat flux sensor is a first heat flux sensor. The sensor main body portion is a first sensor main body portion. The sensor signal is a first sensor signal. In addition to the first heat flux sensor, the measuring instrument includes a second heat flux sensor to be attached to the surface of the human body. The second heat flux sensor includes a film-shaped second sensor main body portion. The second sensor main body portion has a first surface and a second surface on the opposite side of the first surface. The second sensor main body is formed with multiple through holes that penetrate through the second sensor main body portion from the first surface to the second surface. The second sensor main body portion has the first surface on a side adjacent to the human body when in use, and outputs a second sensor signal corresponding to a heat flux passing through the second sensor main body portion from the first surface toward the second surface. A region of the second surface of the second sensor main body portion in which the multiple through holes are formed is exposed to an external space. The calculator calculates the amount of perspiration of the human body based on the first sensor signal and the second sensor signal.

There is a predetermined relationship between the difference between the heat quantities passing through the first sensor main body portion and the second sensor main body portion and the amount of perspiration of the human body. Therefore, with the use of the above relationship, the amount of perspiration from the human body can be calculated based on the respective magnitudes of the first sensor signal and the second sensor signal.

According to a fifth aspect, each of the first sensor main body portion and the second sensor main body portion includes the insulation member, the multiple first thermoelectric members, the multiple second thermoelectric members, the multiple first conductor patterns, and the multiple second conductor patterns. The insulation member is in the form of film having a first surface and a second surface on the opposite side of the first surface, and is flexible. The multiple first thermoelectric members are disposed inside the insulation member and are made of a first thermoelectric material. The multiple second thermoelectric members are disposed inside the insulation member, are made of a second thermoelectric material different from the first thermoelectric material. The multiple first thermoelectric members and the multiple second thermoelectric members are alternately arranged in the insulation member. The multiple first conductor patterns are disposed adjacent to the first surface of the insulation member with respect to the multiple first thermoelectric members and the multiple second thermoelectric members, and each connect the first thermoelectric member and the second thermoelectric member disposed adjacent to each other, among the multiple first thermoelectric members and the multiple second thermoelectric members. The multiple second conductor patterns are disposed adjacent to the second surface of the insulation member with respect to the multiple first thermoelectric members and the multiple second thermoelectric members, and each connect the first thermoelectric member and the second thermoelectric member disposed adjacent to each other, among the multiple first thermoelectric members and the multiple second thermoelectric members. The first surface of the insulation member configures a first surface of each of the first sensor main body portion and the second sensor main body portion. The second surface of the insulation member configures a second surface of each of the first sensor main body portion and the second sensor main body portion. In each of the first sensor main body portion and the second sensor main body portion, the multiple through holes are located in a region of the insulation member where the first thermoelectric member, the second thermoelectric member, the first conductor pattern, and the second conductor pattern are not disposed.

As a specific configuration of each of the first sensor main body portion and the second sensor main body portion, such a configuration can be adopted.

According to a sixth aspect, the moisture absorbing member is a first moisture absorbing member. The first heat flux sensor has a second moisture absorbing member in a form of film capable of absorbing sweat and releasing the absorbed sweat. The second moisture absorbing member is stacked on the first surface of the first sensor main body portion. The second heat flux sensor has a third moisture absorbing member in a form of film capable of absorbing sweat and releasing the absorbed sweat. The third moisture absorbing member is stacked on the first surface of the second sensor main body portion.

According to the above configuration, since the second moisture absorbing member and the third moisture absorbing member are provided, it is less likely that a person to be measured will feel uncomfortable due to the sweat.

What is claimed is:

1. A measuring instrument for measuring a physiological heat quantity emitted from a human body, comprising:
   a heat flux sensor that is to be disposed on a surface of the human body; and
   a calculator that is configured to calculate the physiological heat quantity, wherein
   the heat flux sensor includes a film-shaped sensor main body portion and a film-shaped moisture absorbing member made of a porous material capable of absorbing sweat and releasing the absorbed sweat,
   the sensor main body portion has a first surface and a second surface opposite to the first surface, and is formed with a plurality of through holes penetrating through the sensor main body portion from the first surface to the second surface,
   the sensor main body portion is to be disposed on the surface of the human body such that the first surface is adjacent to the human body when in use, and is configured to output a sensor signal according to a heat flux passing through the sensor main body portion from the first surface toward the second surface,
   the moisture absorbing member is stacked on the second surface of the sensor main body portion,
   the calculator is configured to calculate the physiological heat quantity based on the sensor signal; and
   the sensor main body portion includes:
      a film-shaped insulation member that has a first surface and a second surface opposite to the first surface, and has flexibility,
      a plurality of first thermoelectric members that are disposed inside the insulation member and made of a first thermoelectric material,
      a plurality of second thermoelectric members that are disposed inside the insulation member and arranged alternately with the plurality of first thermoelectric members, and made of a second thermoelectric material different from the first thermoelectric material,
      a plurality of first conductor patterns that are disposed adjacent to the first surface of the insulation member with respect to the plurality of first thermoelectric members and the plurality of second thermoelectric members, the plurality of first conductor patterns each connecting the first thermoelectric member and the second thermoelectric member disposed adjacent to each other among the plurality of first thermoelectric members and the plurality of second thermoelectric members, and
      a plurality of second conductor patterns that are disposed adjacent to the second surface of the insulation member with respect to the plurality of first thermoelectric members and the plurality of second thermoelectric members, the plurality of second conductor patterns each connecting the first thermoelectric member and the second thermoelectric member disposed adjacent to each other among the plurality of first thermoelectric members and the plurality of second thermoelectric members,
      the first surface of the insulation member is the first surface of the sensor main body portion, and the second surface of the insulation member is the second surface of the sensor main body portion, and
      the plurality of through holes are located in a region of the insulation member in which the first thermoelectric members, the second thermoelectric members, the first conductor patterns, and the second conductor patterns are not disposed.

2. The measuring instrument according to claim 1, wherein
   the moisture absorbing member is a first moisture absorbing member,
   the heat flux sensor includes a film-shaped second moisture absorbing member capable of absorbing sweat and releasing the absorbed sweat, and
   the second moisture absorbing member is stacked on the first surface of the sensor main body portion, and is located between the surface of the human body and the sensor main body portion in a state where the heat flux sensor is disposed on the surface of the human body.

3. The measuring instrument according to claim 1, wherein
   the heat flux sensor is a first heat flux sensor,
   the sensor main body portion is a first sensor main body portion, and
   the sensor signal is a first sensor signal,
   the measuring instrument further comprising:
      a second heat flux sensor that is to be disposed on the surface of the human body together with the first heat flux sensor when in use, wherein
   the second heat flux sensor includes a film-shaped second sensor main body portion,
   the second sensor main body portion has a first surface and a second surface opposite to the first surface, and is formed with a plurality of through holes penetrating through the second sensor main body portion from the first surface to the second surface,
   the second sensor main body portion is to be disposed on the surface of the human body such that the first surface is adjacent to the surface of the human body when in use, and is configured to output a second sensor signal according to a heat flux passing through the second sensor main body portion from the first surface side toward the second surface,
   a region of the second surface of the second sensor main body portion formed with the plurality of through holes are exposed to an external space, and
   the calculator is configured to calculate an amount of perspiration of the human body based on the first sensor signal and the second sensor signal.

4. A measuring instrument for measuring a physiological heat quantity emitted from a human body, comprising:
   a heat flux sensor that is to be disposed on a surface of the human body; and
   a calculator that is configured to calculate the physiological heat quantity, wherein
   the heat flux sensor includes a film-shaped sensor main body portion and a film-shaped moisture absorbing member made of a porous material capable of absorbing sweat and releasing the absorbed sweat,
   the sensor main body portion has a first surface and a second surface opposite to the first surface, and is formed with a plurality of through holes penetrating through the sensor main body portion from the first surface to the second surface,
   the sensor main body portion is to be disposed on the surface of the human body such that the first surface is adjacent to the human body when in use, and is configured to output a sensor signal according to a heat flux passing through the sensor main body portion from the first surface toward the second surface, the moisture absorbing member is stacked on the second surface of the sensor main body portion, the calculator is configured to calculate the physiological heat quantity based on the sensor signal, the heat flux sensor is a first heat flux sensor, the sensor main body portion is a first sensor main body portion, the sensor signal is a first sensor signal, the measuring instrument further comprises a second heat flux sensor that is to be disposed on the surface of the human body together with the first heat flux sensor when in use, the second heat flux sensor includes a film-shaped second sensor main body portion, the second sensor main body portion has a first surface and a second surface opposite to the first surface, and is formed with a plurality of through holes penetrating through the second sensor main body portion from the first surface to the second surface, the second sensor main body portion is to be disposed on the surface of the human body such that the first surface is adjacent to the surface of the human body when in use, and is configured to output a second sensor signal according to a heat flux passing through the second sensor main body portion from the first surface side toward the second surface, a region of the second surface of the second sensor main body portion formed with the plurality of through holes are exposed to an external space, and the calculator is configured to calculate an amount of perspiration of the human body based on the first sensor signal and the second sensor signal, each of the first sensor main body portion and the second sensor main body portion includes:

a film-shaped insulation member that has a first surface and a second surface opposite to the first surface, and has flexibility, a plurality of first thermoelectric members that are disposed inside the insulation member, and made of a first thermoelectric material, a plurality of second thermoelectric members that are disposed inside the insulation member and alternately arranged with the plurality of first thermoelectric members, and made of a second thermoelectric material different from the first thermoelectric material, a plurality of first conductor patterns that are disposed adjacent to the first surface of the insulation member with respect to the plurality of first thermoelectric members and the plurality of second thermoelectric members, the plurality of first conductor patterns each connecting the first thermoelectric member and the second thermoelectric member disposed adjacent to each other, among the plurality of first thermoelectric members and the plurality of second thermoelectric members, and a plurality of second conductor patterns that are disposed adjacent to the second surface of the insulation member with respect to the plurality of first thermoelectric members and the plurality of second thermoelectric members, the plurality of second conductor patterns each connecting the first thermoelectric member and the second thermoelectric member disposed adjacent to each other, among the plurality of first thermoelectric members and the plurality of second thermoelectric members, the first surface of the insulation member is the first surface of each of the first sensor main body portion and the second sensor main body portion, and the second surface of the insulation member is the second surface of each of the first sensor main body portion and the second sensor main body portion, and in each of the first sensor main body portion and the second sensor main body portion, the plurality of through holes are located in a region of the insulation member in which the first thermoelectric members, the second thermoelectric members, the first conductor patterns, and the second conductor patterns are not disposed.

5. The measuring instrument according to claim 3, wherein the moisture absorbing member is a first moisture absorbing member, the first heat flux sensor has a film-shaped second moisture absorbing member capable of absorbing sweat and releasing the absorbed sweat, the second moisture absorbing member is stacked on the first surface of the first sensor main body portion, the second heat flux sensor has a film-shaped third moisture absorbing member capable of absorbing sweat and releasing the absorbed sweat, and the third moisture absorbing member is stacked on the first surface of the second sensor main body portion.

6. The measuring instrument according to claim 1, wherein each of the plurality of through holes located in the insulation member provides a hollow space, and an end of the through hole is covered with the moisture absorbing member at the second surface of the insulation member.

7. The measurement instrument according to claim 4, wherein each of the plurality of through holes located in the insulation member provides a hollow space, and an end of the through hole located in the insulation member of the first sensor main body is covered with the moisture absorbing member at the second surface of the insulation member of the first sensor main body.

* * * * *